United States Patent
Yuso

(10) Patent No.: US 7,927,628 B2
(45) Date of Patent: Apr. 19, 2011

(54) SUSTAINED RELEASE PREPARATIONS AND PROCESS FOR PRODUCING THE SAME

(75) Inventor: Tomohira Yuso, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 1174 days.

(21) Appl. No.: 10/504,978

(22) PCT Filed: Feb. 20, 2003

(86) PCT No.: PCT/JP03/01837
§ 371 (c)(1),
(2), (4) Date: Aug. 19, 2004

(87) PCT Pub. No.: WO03/070223
PCT Pub. Date: Aug. 28, 2003

(65) Prior Publication Data
US 2005/0106245 A1    May 19, 2005

(30) Foreign Application Priority Data

Feb. 21, 2002 (JP) ................................. 2002-044460

(51) Int. Cl.
*A61K 9/14* (2006.01)
*A61K 9/16* (2006.01)
*A61K 9/50* (2006.01)

(52) U.S. Cl. ........ 424/495; 424/489; 424/490; 424/493; 424/498; 424/502

(58) Field of Classification Search ................. 424/461, 424/462, 480, 464, 465, 489–502
See application file for complete search history.

(56) References Cited

U.S. PATENT DOCUMENTS 5,266,331 A * 11/1993 Oshlack et al. ............... 424/468
6,245,351 B1 * 6/2001 Nara et al. .................... 424/461

FOREIGN PATENT DOCUMENTS

| EP | 0 508 653 | 3/1992 |
| EP | 0 508 653 | 10/1992 |
| EP | 0 508 653 A1 * | 10/1992 |
| EP | 0 793 959 | 3/1997 |
| EP | 0 793 959 | 9/1997 |
| EP | 0 841 062 A1 * | 5/1998 |
| JP | 62-153213 A | 7/1987 |
| JP | 62-181214 | 8/1987 |
| JP | 04-290817 | 10/1992 |
| JP | 07-316042 A | 12/1995 |
| JP | 2001-106627 | 4/2001 |
| WO | 94/12157 A | 6/1994 |
| WO | WO 00/12064 | 3/2000 |
| WO | 00/69415 A | 11/2000 |

OTHER PUBLICATIONS

Supplementary European Search Report for EPA No. 03742668.1 dated May 13, 2009.

* cited by examiner

*Primary Examiner* — Michael G Hartley
*Assistant Examiner* — Micah-Paul Young
(74) *Attorney, Agent, or Firm* — Sughrue Mion, PLLC

(57) ABSTRACT

The present invention provides sustained-release preparations from which a pharmacologically active substance can be released over a long time and a process for producing the same. Such a sustained-release preparation is produced by melt-granulating a low-melting-point substance and a pharmacologically active substance and melt-coating the surface of the thus obtained particles with (1) a fine powder of a water-insoluble polymer or (2) a fine powder of a water-insoluble polymer and at least one member selected from the group consisting of talc, magnesium stearate and titanium oxide.

2 Claims, 2 Drawing Sheets

SUSTAINED RELEASE PREPARATIONS AND PROCESS FOR PRODUCING THE SAME

This application is a 371 of PCT/JP03/01837, filed Feb. 20, 2003, the disclosure of which is incorporated herein by reference.

TECHNICAL FIELD

The present invention relates to sustained-release preparations and methods for producing the same.

BACKGROUND ART

Low-melting-point substances, for example, wax-like substances, glycerine fatty acid esters, etc., are used in fields such as sustained-release preparations and preparations for masking bitterness.

For example, the specification of Japanese patent No. 3130058 discloses granules obtained by melt-granulating a powdered or granular water-insoluble low-melting-point substance, a powdered or granular disintegrator and a powdered drug having an unpleasant taste, and melting the thus obtained granules at a temperature not less than the melting point of the low-melting-point substance with a fine powder additive under flow conditions. The fine powder additives disclosed in the above-mentioned patent specification include talc, light anhydrous silicic acid, magnesium metasilicate aluminate, calcium stearate, magnesium stearate, titanium oxide, synthetic aluminum silicate, etc.

Specification of Japanese patent No. 2915653 discloses granules obtained by melt-granulating a powdered or granular drug having bitterness and a powdered or granular water-insoluble polymer selected from the group consisting of acrylic polymers, cellulose-based polymers, and their mixture, with a powdered or granular water-soluble low-melting-point substance having a melting point of 40-90° C.

However, the granules disclosed in these patent specifications are prepared so as to mask the unpleasant taste of a drug with the drug being immediately released. The granules disclosed in these patent specifications are fast released and do not have sustained-release properties.

Regarding sustained-release preparations, Japanese Unexamined Patent Publication No. 2001-278781 discloses a sustained-release preparation and a preparation method thereof, wherein a drug-containing core material having a particle diameter of not greater than 200 μm is spray-coated with a liquid obtained by dissolving a mixture of a hydrophobic organic compound and a water soluble polymer in an organic solvent, and the spray-coated layer is further spray-coated with a different liquid obtained by dissolving a mixture of a hydrophobic organic compound and a water soluble polymer in an organic solvent.

Because the method disclosed in Japanese Unexamined Patent Publication No. 2001-278781 employs spray coating, the use of an alcohol, ketone, halogenated hydrocarbon, ester, ether or like organic solvent is crucial. Use of such organic solvents adversely affects the human body, etc., both during the production of such preparations and when administered.

DISCLOSURE OF THE INVENTION

An object of the present invention is to provide a sustained-release preparation from which a pharmacologically active substance can be released over a long period of time.

Another object of the present invention is to provide a method for producing a sustained-release preparation that does not adversely affect the human body, etc.

The present inventors conducted intensive research to achieve the above objects and found that a sustained-release preparation that can release a pharmacologically active substance over a long time can be produced by melt-coating the surface of particles with a specific fine powder, the particles being obtained by melt-granulating a low-melting-point substance and a pharmacologically active substance. The present invention has been accomplished based on the above finding.

1. The present invention provides a sustained-release preparation produced by melt-granulating a low-melting-point substance and a pharmacologically active substance, and melt-coating the surface of the thus obtained particles with (1) a fine powder of a water-insoluble polymer or (2) a fine powder of a water-insoluble polymer and at lest one member selected from the group consisting of talc, magnesium stearate and titanium oxide.

2. The present invention provides a sustained-release preparation according to Item 1, wherein the content of water-insoluble polymer in the fine powder of (2) is not less than 10 wt. %.

3. The present invention provides a sustained-release preparation according to Item 1 or 2, wherein the water-insoluble polymer is at least one member selected from the group consisting of ethylcellulose and cellulose acetate.

4. The present invention provides a sustained-release preparation according to Item 1 or 2, wherein the water-insoluble polymer is ethylcellulose.

5. The present invention provides a method for producing a sustained-release preparation comprising the steps of:

melt-granulating a low-melting-point substance and a pharmacologically active substance; and melt-coating the surface of the thus obtained particles with (1) a fine powder of a water-insoluble polymer or (2) a fine powder of a water-insoluble polymer and at least one member selected from the group consisting of talc, magnesium stearate and titanium oxide.

6. The present invention provides a sustained-release preparation produced by dissolving or dispersing a pharmacologically active substance in a molten mixture of a low-melting-point substance and a pH-independent water-insoluble polymer, spraying and cooling the resulting liquid to obtain particles, and melt-coating the surface of the thus obtained particles with (1) a fine powder of a water-insoluble polymer or (2) a fine powder of a water-insoluble polymer and at least one member selected from the group consisting of talc, magnesium stearate and titanium oxide.

7. The present invention provides a sustained-release preparation according to Item 6, wherein the content of water-insoluble polymer in the fine powder of (2) is not less than 10 wt. %.

8. The present invention provides a sustained-release preparation according to Item 6 or 7, wherein the water-insoluble polymer is at least one member selected from the group consisting of ethylcellulose and cellulose acetate.

9. The present invention provides a sustained-release preparation according to Item 6 or 7, wherein the water-insoluble polymer is ethylcellulose.

10. The present invention provides a method for producing a sustained-release preparation comprising the steps of:

dissolving or dispersing a pharmacologically active substance in a molten mixture of a low-melting-point substance and a pH-independent water-insoluble polymer;

spraying and cooling the resulting liquid to obtain particles; and melt-coating the surface of the thus obtained particles with (1) a fine powder of a water-insoluble polymer or (2) a fine powder of a water-insoluble polymer and at least one member selected from the group consisting of talc, magnesium stearate and titanium oxide.

11. The present invention provides a sustained-release preparation produced by melt-granulating a low-melting-point substance and a pharmacologically active substance, melt-coating the surface of the thus obtained particles with (1) a fine powder of a water-insoluble polymer or (2) a fine powder of a water-insoluble polymer and at least one member selected from the group consisting of talc, magnesium stearate and titanium oxide, and then adhering a powder of at least one member selected from the group consisting of lactose, talc, magnesium stearate and titanium oxide to the melt-coated surface.

12. The present invention provides a sustained-release preparation according to Item 11, wherein the content of the water-insoluble polymer in the fine powder of (2) is not less than 10 wt. %.

13. The present invention provides a sustained-release preparation according to Item 11 or 12, wherein the water-insoluble polymer is at least one member selected from the group consisting of ethylcellulose and cellulose acetate.

14. The present invention provides a sustained-release preparation according to Item 11 or 12, wherein the water-insoluble polymer is ethylcellulose.

15. The present invention provides a method for producing a sustained-release preparation comprising the steps of:

melt-granulating a low-melting-point substance and a pharmacologically active substance;

melt-coating the surface of the thus obtained particles with (1) a fine powder of a water-insoluble polymer or (2) a fine powder of a water-insoluble polymer and at least one member selected from the group consisting of talc, magnesium stearate and titanium oxide; and adhering a powder of at least one member selected from the group consisting of lactose, talc, magnesium stearate and titanium oxide to the thus-formed melt-coated surface.

16. The present invention provides a sustained-release preparation produced by dissolving or dispersing a pharmacologically active substance in a molten mixture of a low-melting-point substance and a pH-independent water-insoluble polymer; spraying and cooling the resulting liquid to obtain particles; melt-coating the surface of the thus obtained particles with (1) a fine powder of a water-insoluble polymer or (2) a fine powder of a water-insoluble polymer and at least one member selected from the group consisting of talc, magnesium stearate and titanium oxide; and adhering a powder of at least one member selected from the group consisting of lactose, talc, magnesium stearate and titanium oxide to the melt-coated surface.

17. The present invention provides a sustained-release preparation according to Item 16, wherein the content of the water-insoluble polymer in the fine powder of (2) is not less than 10 wt. %.

18. The present invention provides a sustained-release preparation according to Item 16 or 17, wherein the water-insoluble polymer is at least one member selected from the group consisting of ethylcellulose and cellulose acetate.

19. The present invention provides a sustained-release preparation according to Item 16 or 17, wherein the water-insoluble polymer is ethylcellulose.

20. The present invention provides a method for producing a sustained-release preparation comprising the steps of:

dissolving or dispersing a pharmacologically active substance in a molten mixture of a low-melting-point substance and a pH-independent water-insoluble polymer;

spraying and cooling the resulting liquid to obtain particles;

melt-coating the surface of the thus obtained particles with (1) a fine powder of a water-insoluble polymer or (2) a fine powder of a water-insoluble polymer and at least one member selected from the group consisting of talc, magnesium stearate and titanium oxide; and adhering a powder of at least one member selected from the group consisting of lactose, talc, magnesium stearate and titanium oxide to the thus-formed melt-coated surface.

21. The present invention provides a sustained-release preparation produced by melt-granulating a low-melting-point substance and a pharmacologically active substance to obtain particles;

melt-coating the surface of the thus obtained particles with (1) a fine powder of a water-insoluble polymer or (2) a fine powder of a water-insoluble polymer and at least one member selected from the group consisting of talc, magnesium stearate and titanium oxide; and coating the thus-formed melt-coated surface with (3) a fine powder of a pH-dependent polymer that is gastric or enteric or (4) a fine powder of the pH-dependent polymer and at least one member selected from the group consisting of talc, magnesium stearate and titanium oxide.

22. The present invention provides a sustained-release preparation according to Item 21, wherein the content of the water-insoluble polymer in the fine powder of (2) is not less than 10 wt. %.

23. The present invention provides a sustained-release preparation according to Item 21 or 22, wherein the water-insoluble polymer is at least one member selected from the group consisting of ethylcellulose and cellulose acetate.

24. The present invention provides a sustained-release preparation according to Item 21 or 22, wherein the water-insoluble polymer is ethylcellulose.

25. The present invention provides a method for producing a sustained-release preparation comprising the steps of:

melt-granulating a low-melting-point substance and a pharmacologically active substance to obtain particles;

melt-coating the surface of the thus obtained particles with (1) a fine powder of a water-insoluble polymer or (2) a fine powder of a water-insoluble polymer and at least one member selected from the group consisting of talc, magnesium stearate and titanium oxide; and coating the thus-formed melt-coated surface with (3) a fine powder of a pH-dependent polymer that is gastric or enteric or (4) a fine powder of the pH-dependent polymer and at least one member selected from the group consisting of talc, magnesium stearate and titanium oxide.

26. The present invention provides a method for producing a sustained-release preparation according to Item 25, wherein the coating with the fine powder of (3) or (4) is conducted by spray coating.

27. The present invention provides a sustained-release preparation produced by dissolving or dispersing a pharmacologically active substance in a molten mixture of a low-melting-point substance and a pH-independent water-insoluble polymer; spraying and cooling the resulting liquid to obtain particles; melt-coating the surface of the thus obtained particles with (1) a fine powder of a water-insoluble polymer or (2) a fine powder of a water-insoluble polymer and at least one member selected from the group consisting of talc, magnesium stearate and titanium oxide; and coating the thus-formed melt-coated surface with (3) a fine powder of a pH-dependent polymer that is gastric or enteric or (4) a fine powder of the pH-dependent polymer and at least one member selected from the group consisting of talc, magnesium stearate and titanium oxide.

28. The present invention provides a sustained-release preparation according to Item 27, wherein the content of the water-insoluble polymer in the fine powder of (2) is not less than 10 wt. %.

29. The present invention provides a sustained-release preparation according to Item 27 or 28, wherein the water-insoluble polymer is at least one member selected from the group consisting of ethylcellulose and cellulose acetate.

30. The present invention provides a sustained-release preparation according to Item 27 or 28, wherein the water-insoluble polymer is ethylcellulose.

31. The present invention provides a method for producing a sustained-release preparation comprising the steps of:

dissolving or dispersing a pharmacologically active substance in a molten mixture of a low-melting-point substance and a pH-independent water-insoluble polymer;

spraying and cooling the resulting liquid to obtain particles;

melt-coating the surface of the thus obtained particles with (1) a fine powder of a water-insoluble polymer or (2) a fine powder of a water-insoluble polymer and at least one member selected from the group consisting of talc, magnesium stearate and titanium oxide; and coating the thus-formed melt-coated surface with (3) a fine powder of a pH-dependent polymer that is gastric or enteric or (4) a fine powder of the pH-dependent polymer and at least one member selected from the group consisting of talc, magnesium stearate and titanium oxide.

32. The present invention provides a method for producing a sustained-release preparation according to Item 31, wherein the coating with the fine powder of (3) or (4) is conducted by spray coating.

33. The present invention provides a sustained-release preparation produced by melt-granulating a low-melting-point substance and a pharmacologically active substance; melt-coating the surface of the thus obtained particles with (1) a fine powder of a water-insoluble polymer or (2) a fine powder of a water-insoluble polymer and at least one member selected from the group consisting of talc, magnesium stearate and titanium oxide; adhering a powder of at least one member selected from the group consisting of lactose, talc, magnesium stearate and titanium oxide to the thus-formed melt-coated surface; and further applying a coating of (3) a fine powder of a pH-dependent polymer that is gastric or enteric or (4) a fine powder of the pH-dependent polymer and at least one member selected from the group consisting of talc, magnesium stearate and titanium oxide.

34. The present invention provides a sustained-release preparation according to Item 33, wherein the content of the water-insoluble polymer in the fine powder of (2) is not less than 10 wt. %.

35. The present invention provides a sustained-release preparation according to Item 33 or 34, wherein the water-insoluble polymer is at least one member selected from the group consisting of ethylcellulose and cellulose acetate.

36. The present invention provides a sustained-release preparation according to Item 33 or 34, wherein the water-insoluble polymer is ethylcellulose.

37. The present invention provides a method for producing a sustained-release preparation comprising the steps of:

melt-granulating a low-melting-point substance and a pharmacologically active substance to obtain particles;

melt-coating the surface of the thus obtained particles with (1) a fine powder of a water-insoluble polymer or (2) a fine powder of a water-insoluble polymer and at least one member selected from the group consisting of talc, magnesium stearate and titanium oxide;

adhering a powder of at least one member selected from the group consisting of lactose, talc, magnesium stearate and titanium oxide to the thus-formed melt-coated surface; and further applying a coating of (3) a fine powder of a pH-dependent polymer that is gastric or enteric or (4) a fine powder of the pH-dependent polymer and at least one member selected from the group consisting of talc, magnesium stearate and titanium oxide.

38. The present invention provides a method for producing a sustained-release preparation according to Item 37, wherein the coating of the fine powder of (3) or (4) is applied by spray coating.

39. The present invention provides a sustained-release preparation produced by dissolving or dispersing a pharmacologically active substance in a molten mixture of a low-melting-point substance and a pH-independent water-insoluble polymer; spraying and cooling the resulting liquid to obtain particles; melt-coating the surface of the thus obtained particles with (1) a fine powder of a water-insoluble polymer or (2) a fine powder of a water-insoluble polymer and at least one member selected from the group consisting of talc, magnesium stearate and titanium oxide; adhering a powder of at least one member selected from the group consisting of lactose, talc, magnesium stearate and titanium oxide to the thus-formed melt-coated surface; and further applying a coating of (3) a fine powder of the above mentioned pH-dependent polymer and a pH-dependent polymer that is gastric or enteric or (4) a fine powder of at least one member selected from the group consisting of talc, magnesium stearate and titanium oxide.

40. The present invention provides a sustained-release preparation according to Item 39, wherein the content of the water-insoluble polymer in the fine powder of (2) is not less than 10 wt. %.

41. The present invention provides a sustained-release preparation according to Item 39 or 40, wherein the water-insoluble polymer is at least one member selected from the group consisting of ethylcellulose and cellulose acetate.

42. The present invention provides a sustained-release preparation according to Item 39 or 40, wherein the water-insoluble polymer is ethylcellulose.

43. The present invention provides a method for producing a sustained-release preparation comprising the steps of:

dissolving or dispersing a pharmacologically active substance in a molten mixture of a low-melting-point substance and a pH-independent water-insoluble polymer;

spraying and cooling the resulting liquid to obtain particles;

melt-coating the surface of the thus obtained particles with (1) a fine powder of a water-insoluble polymer or (2) a fine powder of a water-insoluble polymer and at least one member selected from the group consisting of talc, magnesium stearate and titanium oxide;

adhering a powder of at least one member selected from the group consisting of lactose, talc, magnesium stearate and titanium oxide to the melt-coated surface; and further applying a coating of (3) a fine powder of a pH-dependent polymer that is gastric or enteric or (4) a fine powder of the pH-dependent polymer and at least one member selected from the group consisting of talc, magnesium stearate and titanium oxide.

44. The present invention provides a method for producing a sustained-release preparation according to Item 43, wherein the coating of the fine powder of (3) or (4) is applied by spray coating.

45. The present invention provides a sustained-release preparation produced by melt-granulating a low-melting-point substance and a pharmacologically active substance; melt-coating the surface of the thus obtained particles with (1) a fine powder of a water-insoluble polymer or (2) a fine powder of a water-insoluble polymer and at least one member selected from the group consisting of talc, magnesium stearate and titanium oxide; melt-coating the melt-coated surface with (3) a fine powder of a pH-dependent polymer that is gastric or enteric or (4) a fine powder of the pH-dependent polymer and at least one member selected from the group consisting of talc, magnesium stearate and titanium oxide; and further adhering a powder of at least one member selected from the group consisting of lactose, talc, magnesium stearate and titanium oxide thereonto.

46. The present invention provides a sustained-release preparation according to Item 45, wherein the content of the water-insoluble polymer in the fine powder of (2) is not less than 10 wt. %.

47. The present invention provides a sustained-release preparation according to Item 45 or 46, wherein the water-insoluble polymer is at least one member selected from the group consisting of ethylcellulose and cellulose acetate.

48. The present invention provides a sustained-release preparation according to Item 45 or 46, wherein the water-insoluble polymer is ethylcellulose.

49. The present invention provides a sustained-release preparation of Item 45 that is produced by dissolving or dispersing a pharmacologically active substance in a molten mixture of a low-melting-point substance and a pH-independent water-insoluble polymer; spraying and cooling the resulting liquid to obtain particles; melt-coating the surface of the thus obtained particles with (1) a fine powder of a water-insoluble polymer or (2) a fine powder of a water-insoluble polymer and at least one member selected from the group consisting of talc, magnesium stearate and titanium oxide; further melt-coating the thus-formed melt-coated surface with (3) a fine powder of a pH-dependent polymer that is gastric or enteric or (4) a fine powder of the pH-dependent polymer and at least one member selected from the group consisting of talc, magnesium stearate and titanium oxide, and adhering a powder of at least one member selected from the group consisting of lactose, talc, magnesium stearate and titanium oxide thereonto.

50. The present invention provides a sustained-release preparation according to Item 49, wherein the content of the water-insoluble polymer in the fine powder of (2) is not less than 10 wt. %.

51. The present invention provides a sustained-release preparation according to Item 49 or 50, wherein the water-insoluble polymer is at least one member selected from the group consisting of ethylcellulose and cellulose acetate.

52. The present invention provides a sustained-release preparation according to Item 49 or 50, wherein the water-insoluble polymer is ethylcellulose.

53. The present invention provides a method for producing a sustained-release preparation of Item 45 comprising the steps of:
melt-granulating a low-melting-point substance and a pharmacologically active substance;
melt-coating the surface of the thus obtained particles with (1) a fine powder of a water-insoluble polymer or (2) a fine powder of a water-insoluble polymer and at least one member selected from the group consisting of talc, magnesium stearate and titanium oxide;
melt-coating the thus-formed melt-coated surface with (3) a fine powder of a pH-dependent polymer that is gastric or enteric or (4) a fine powder of the pH-dependent polymer and at least one member selected from the group consisting of talc, magnesium stearate and titanium oxide; and
further adhering a powder of at least one member selected from the group consisting of lactose, talc, magnesium stearate and titanium oxide thereto.

54. The present invention provides a method for producing a sustained-release preparation of Item 49 comprising the steps of:
dissolving or dispersing a pharmacologically active substance in a molten mixture of a low-melting-point substance and a pH-independent water-insoluble polymer;
spraying and cooling the resulting liquid to obtain particles;
melt-coating the surface of the thus obtained particles with (1) a fine powder of a water-insoluble polymer or (2) a fine powder of a water-insoluble polymer and at least one member selected from the group consisting of talc, magnesium stearate and titanium oxide;
further melt-coating the thus-formed melt-coated surface with (3) a fine powder of a pH-dependent polymer that is gastric or enteric or (4) a fine powder of the pH-dependent polymer and at least one member selected from the group consisting of talc, magnesium stearate and titanium oxide, and
adhering a powder of at least one member selected from the group consisting of lactose, talc, magnesium stearate and titanium oxide thereto.

The pharmacologically active substances used in the sustained-release preparations of the present invention are not limited and various kinds of pharmaceutical preparations generally used in this field may be used. Examples of usable pharmacologically active substances include those generally used in various kinds of pharmaceutical preparations, such as, respiratory drugs, gastrointestinal drugs, circulatory drugs, central nervous system drugs, peripheral nervous system drugs, antibiotics, chemotherapeutics, antitumor agents, platelet aggregation inhibitors, anti-allergy agents, vitamin preparations, etc. Specific examples of such pharmacologically active substances include theophylline, cilostazol, grepafloxacin, carteolol, procaterol, rebamipide, aripiprazole, etc.

Various kinds of pharmaceutically acceptable water-insoluble or poorly water-soluble substances may be used as low-melting-point substances, including surfactants such as glycerol fatty acid esters, polyglycerol fatty acid esters, glycerol fatty acids and citric acid and like glycerol fatty acids and organic acids; stearic acid, palmitic acid and like higher fatty acids; stearyl alcohol, cetanol and like higher alcohols. These low-melting-point substances may be used singly or in a combination of two or more.

Among such above-mentioned low-melting-point substances, glycerol fatty acid esters, polyglycerol fatty acid esters, glycerol fatty acids and citric acid and like glycerol fatty acids and organic acids are preferable and glycerol fatty acid esters are the most preferable. Glycerol behenates and glycerol stearates are preferable as glycerol fatty acid esters. Tetraglycerol hexabehenate is preferable as a polyglycerol fatty acid ester.

Among the low-melting-point substances, those having a melting point in the range of from about 40 to about 90° C. are preferable and those having a melting point in the range of from about 50 to about 80° C. are more preferable.

Sustained-release preparations of the present invention can be prepared by, for example, melt-coating the surface of particles with a specific fine powder, the particles being obtained by melt-granulating a low-melting-point substance and a pharmacologically active substance.

Production of Particles

The particles (core particles) to be melt-coated can be obtained by, for example, melt-granulating a low-melting-point substance and a pharmacologically active substance. More specifically, particles to be melt-coated can be obtained by melting a low-melting-point substance, dissolving or dispersing a pharmacologically active substance in the melt, spraying the dissolved or dispersed solution, and cooling the resulting particles.

The temperature at the time of melting the low-melting-point substance is set at or higher than the melting point of the low-melting-point substance, preferably higher than its melting point by 10° C. or more, provided the temperature does not adversely affect the stability of the pharmacologically active substance. The temperature is generally about 90 to about 150° C. and preferably about 100 to about 140° C.

The pharmacologically active substance is used in the form of a powder having an average particle diameter of about 0.1 to 100 µm, and preferably about 0.5 to 50 µm.

The low-melting-point substance is generally used in an amount of 50 to $1 \times 10^5$ wt. %, preferably 75 to $3 \times 10^4$ wt. %, and more preferably 100 to $1 \times 10^4$ wt. %, relative to the pharmacologically active substance.

In the present invention, it is preferable that for preparing particles a pH-independent water-insoluble polymer be used together with a low-melting-point substance and a pharmacologically active substance.

Various kinds of known water-insoluble polymers having pH-independent properties can be used as pH-independent water-insoluble polymers. Usable pH-independent water-insoluble polymers include ethylcellulose, aminoalkyl methacrylate copolymer RS, aminoalkyl methacrylate copolymer RL, cellulose acetate, cellulose acetate butyrate, and cellulose acetate propionate, etc. Specific examples of aminoalkyl methacrylate copolymer RS include Eudragit RS-100, Eudragit RS-PO, etc. Specific examples of aminoalkyl methacrylate copolymer RL include Eudragit RL-100, Eudragit RL-PO, etc.

These pH-independent water-insoluble polymers may be used singly or in a combination of two or more. Among the above-mentioned pH-independent water-insoluble polymers, ethylcellulose, aminoalkyl methacrylate copolymer RS and aminoalkyl methacrylate copolymer RL are preferable.

The pH-independent water-insoluble polymers, when employed, are used in an amount of generally 0.5 to 60 wt. %, preferably 1 to 50 wt. %, and more preferably 1 to 45 wt. %, relative to the low-melting-point substance.

When pH-independent water-insoluble polymers are used, the above-mentioned particles are obtained by melting a low-melting-point substance, dissolving or dispersing a pharmacologically active substance and a pH-independent water-insoluble polymer in the melt, spraying the resulting solution or dispersion, followed by cooling.

The order of addition of the pharmacologically active substance and the pH-independent water-insoluble polymer to the melt of the low-melting-point substance is not particularly limited. It is possible to dissolve (melt) the pH-independent water-insoluble polymer after dissolving or dispersing the pharmacologically active substance in the melt, or to dissolve or disperse a pharmacologically active substance after dissolving (melting) the pH-independent water-insoluble polymer in the melt. Alternatively, dissolution or dispersion of the pharmacologically active substance in the melt and dissolution (melting) of a pH-independent water-insoluble polymer in the melt substance may be conducted simultaneously.

A preferable method is that the particles are obtained by melting a low-melting-point substance, adding a pH-independent water-insoluble polymer to the melt and dissolving (melting) it, thereafter dissolving or dispersing a pharmacologically active substance in the thus obtained liquid, spraying the resulting solution or dispersion, followed by cooling.

Spraying of the solution or dispersion may be conducted by known methods. By suitably selecting spraying conditions, it is possible to control the desired particle size. The particle thus obtained can be sized using a sieve, etc.

The average particle diameter is generally about 10 to about 1400 µm and preferably about 20 to about 1000 µm. Fine particles having an average particle diameter of about 50 to about 600 µm are especially preferable. The average particle diameter can be measured by known methods such as sieving.

Melt-Coating

Sustained-release preparations of the present invention is produced by melt-coating the above-obtained particles with a specific fine powder, i.e., (1) a fine powder of a water-insoluble polymer or (2) a fine powder of a water-insoluble polymer and at least one member selected from the group consisting of talc, magnesium stearate and titanium oxide. Unlike spray coating, no organic solvent is used during melt-coating.

When the particles obtained by melt-granulation are subjected to melting again, low-melting-point substances remaining inside particles percolate towards the particle surface. Due to the adhesion ability of the melt, any fine powder in the vicinity adheres to this percolating melt. Melt-coating of the present invention is a technique for forming a coating layer on the surface of granulated particles using the above-mentioned property of the low-melting-point substance.

When fine powder (2) is used, the content of the water-insoluble polymer in the fine powder is generally not less than 10 wt. %, preferably not less than 40 wt. %, more preferably not less than 50 wt. % and still more preferably not less than 60 wt. %.

Examples of the water-insoluble polymers include ethylcellulose, cellulose acetate, etc., with ethylcellulose being preferable among them.

The size of the fine powder varies depending on the particle size to be melt-coated. Generally the size of the fine powder is smaller than that of the particles.

The average particle diameter of the fine powder can be selected depending on the size of the sustained-release preparation to be produced and is generally not more than about 40 µm, preferably about 1 to about 30 µm and more preferably about 1 to about 25 µm.

Melt-coating can be conducted by known methods. For example, the above-mentioned specific fine powder is mixed with the above-obtained particles and the mixture is agitated with heating.

The amount of the fine powder is, based on 100 parts by weight of the particles, generally 0.2 to 100 parts by weight and preferably 0.4 to 70 parts by weight.

The heating temperature is set at or higher than the temperature at which the low-melting-point substance softens or melts, specifically in the range of from about 40 to about 90° C.

Agitation may be conducted by ordinary stirring methods.

Particles having fine powder melt-coated on their surface are thus produced. Such a particle having been subjected to melt-coating is hereunder termed "coated particle I".

Preferable example of melt-coating is described below. Predetermined amounts of particle and fine powder are put into a granulator mixer equipped with a jacket and then mixed. By stirring the mixture at the jacket temperature of about 40 to about 90° C. (preferably 50 to 77° C. and more preferably 60 to 75° C.), the particle surface is softened and becomes adhesive, and the fine powder is thereby adhered to the surface of the particle.

It is preferable that one or more other suitable powders be added when the fine powder is uniformly adhered over substantially the entire surface of the particle and stirring be continued while lowering the jacket temperature. The thus obtained particles that have been subjected to further melt-coating are hereunder termed "coated particle II".

The powders added thereto can be selected from those various types that do not adversely affect the sustained-release properties of the preparation, and include lactose, talc, magnesium stearate, titanium oxide, etc. These may be used singly or in a combination of two or more.

The average particle diameter of the powder may be of the same order as that of the fine powder, and is generally not more than 40 μm, preferably about 1 to about 30 μm and more preferably about 1 to about 25 μm.

The powder is adhered to the surface of the melt-coated particles by suitably controlling the temperature and the amount to be added. The amount of the powder to be adhered is generally 1 to 90 wt. %, preferably 10 to 70 wt. %, and more preferably 10 to 50 wt. %, relative to the melt-coated particles. The powder may be adhered to the entire surface of the melt-coated particle or may be adhered to only a portion of the surface of the melt-coated particle.

The average particle diameter of the above-obtained coated particles (coated particle I and coated particle II) is generally about 11 to about 1500 μm, preferably about 21 to 1100 μm, more preferably about 51 to 650 μm and particularly preferably about 90 to about 200 μm.

The above-obtained coated particles can be sized using a sieve, etc.

The sustained-release preparation of the present invention is thus produced.

Multi-Layer Coating

The sustained-release preparation of the present invention may further comprise, on the surface of the coated particle (coated particle I or coated particle II), a coating of (3) a fine powder of a gastric or enteric pH-dependent polymer or (4) a fine powder of the pH-dependent polymer and at least one member selected from the group consisting of talc, magnesium stearate and titanium oxide.

Various known gastric or enteric pH-dependent polymers can be used.

Examples of gastric pH-dependent polymers include gastric polyvinyl derivatives, gastric acrylic acid-based copolymers, etc.

Specific examples of gastric polyvinyl derivatives include polyvinylacetal, diethylaminoacetate, etc.

Specific examples of gastric acrylic acid-based copolymers include methyl methacrylate-butyl methacrylate-dimethylaminoethyl methacrylate copolymers (for example, product name: Eudragit E, etc.), etc.

Examples of enteric pH-dependent polymers include enteric cellulose derivatives, enteric acrylic acid-based copolymers, enteric maleic acid-based copolymers, enteric polyvinyl derivatives, etc.

Specific examples of enteric cellulose derivatives include hydroxypropylmethylcellulose acetate succinate, hydroxypropylmethylcellulose phthalate, hydroxymethylethylcellulose phthalate, cellulose acetate phthalate, cellulose acetate succinate, cellulose acetate maleate, cellulose benzoate phthalate, cellulose propionate phthalate, methylcellulose phthalate, carboxymethylethylcellulose, ethylhydroxyethylcellulose phthalate, etc.

Specific examples of enteric acrylic acid-based copolymers include styrene-acrylic acid copolymers, methyl acrylate-acrylic acid copolymers, methyl acrylate-methacrylic acid copolymers, butyl acrylate-styrene-acrylic acid copolymers, methacrylic acid-methyl methacrylate copolymers (for example, product name: Eudragit L100, Eudragit S, etc.), methacrylic acid-ethyl acrylate copolymers (for example, product name: Eudragit L100-55, etc.) methyl acrylate-methacrylic acid-octyl acrylate copolymers, etc.

Specific examples of enteric maleic acid-based copolymers include vinyl acetate-maleic anhydride copolymers, styrene-maleic anhydride copolymers, styrene-maleic monoester copolymers, vinyl methyl ether-maleic anhydride copolymers, ethylene-maleic anhydride copolymers, vinyl butyl ether-maleic anhydride copolymers, acrylonitrile-methyl acrylate-maleic anhydride copolymers, butyl acrylate-styrene-maleic anhydride copolymers, etc.

Specific examples of enteric polyvinyl derivatives include polyvinyl alcohol phthalate, polyvinyl acetal phthalate, polyvinyl butyrate phthalate, polyvinyl acetoacetal phthalate, etc.

The above-mentioned gastric or enteric pH-dependent polymers may be used singly or in a combination of two or more.

The amount of the gastric or enteric pH-dependent polymer used is generally 4 to 100 wt. %, preferably 5 to 90 wt. % and more preferably 6 to 80 wt. % relative to the coated particles.

When fine powder (4) is used, the content of pH-dependent polymer in the fine powder is generally not less than 1 wt. %, preferably not less than 5 wt. % and more preferably not less than 10 wt. %.

To coat the surface of the coated particle (coated particle I or coated particle II) with the fine powder (3) or (4), various known coating methods can be used. Examples of coating methods include spray coating, etc.

The multicoated sustained-release preparation is obtained by melt-coating the above-mentioned specific fine powder on the surface of the particles, and melt-coating the particles with (3) a fine powder of a gastric or enteric pH-dependent polymer or (4) a fine powder of the pH-dependent polymer and at least one member selected from the group consisting of talc, magnesium stearate and titanium oxide.

A preferable example of multilayer melt-coating is explained below. Predetermined amounts of particle and fine powder (1) or (2) are placed in a granulator mixer equipped with a jacket and then mixed. By stirring the mixture at a jacket temperature of about 40 to about 90° C. (preferably 50 to 77° C. and more preferably 60 to 75° C.), the particle surface is softened to have the adhesiveness, and the fine powder (1) or (2) is thereby coated onto the surface of the particle. Thereafter, a predetermined amount of fine powder (3) or (4) is placed in the granulator mixer equipped with a jacket and then mixed. By stirring the mixture at a jacket temperature of about 40 to about 90° C. (preferably 50 to 77° C. and more preferably 60 to 75° C.), the particle surface is softened to have the adhesiveness, and the fine powder (3) or (4) is thereby coated onto the surface of the particle. Multilayer-coated sustained-release preparations are thus produced.

It is preferable that one or more other suitable powders be added when fine powder is uniformly adhered over substantially the entire surface of the particle and stirring be continued while lowering the jacket temperature.

The powder to be added thereto can be selected from those various types that do not adversely affect the sustained-release properties of the preparation, and include lactose, talc, magnesium stearate, titanium oxide, etc. These may be used singly or in a combination of two or more.

The average particle diameter of the powder may be generally not more than 40 μm, preferably about 1 to about 30 μm and more preferably about 1 to about 25 μm.

The powder is adhered to the surface of the melt-coated particle by suitably controlling the temperature and the amount to be added. The amount of the powder to be adhered is generally 1 to 90 wt. %, preferably 10 to 70 wt. %, and more preferably 10 to 50 wt. %, relative to the melt-coated particles. The powder may be adhered to the entire surface of the melt-coated particle or may be adhered to only a portion of the surface of the melt-coated particle.

The average particle diameter of the above-obtained multicoated particle is generally about 12 to about 1600 μm, preferably about 22 to about 1200 μm, more preferably about 52 to about 1700 μm and particularly preferably about 95 to about 210 μm.

The above-obtained multicoated particles can be sized using a sieve, etc.

The sustained-release preparation of the present invention is thus produced.

In the present invention, by adding excipients, binders, disintegrators, sweetening agents, coloring agents, free-flow agents, lubricants and like pharmaceutical carriers, the melt-coated particles or multicoated particles can be formulated into powders, granules, dry-syrups, tablets, capsules, etc.

Various excipients generally used in this field can be used. For example, mannitol, sorbitol, xylitol, erythritol, maltitol, glucose, saccharose, lactose and like saccharides; cornstarch, potato starch and like starches; anhydrous calcium hydrogenphosphate, calcium phosphate and like inorganic salts; crystalline cellulose, sodium carboxymethyl starch, dextrin, macrogol (for example, polyethylene glycol 6000, polyethylene glycol 4000, etc.), etc.

As a binder, various kinds of publicly known ones can be used, including methylcellulose, hydroxypropyl cellulose, hydroxypropylmethylcellulose, polyvinyl pyrrolidone, gelatin, gum arabic, polyvinyl alcohol, pullulan, macrogoal (for example, polyethylene glycol 6000, polyethylene glycol 4000, etc.), α starch, partly pregelatinized starch, etc.

Examples of usable disintegrators include those typically used in this field, such as low-substituted hydroxypropyl cellulose, sodium carboxymethyl starch, croscarmellose sodium, carboxymethylcellulose, crystalline cellulose, crospovidone, etc.

Various sweetening agents generally used in this field can be used, including aspartame, fructoses, xylitol, saccharin, sodium saccharin, saccharose, purified saccharose, sorbitol, lactose, glucose, mannitol, thaumatin, erythritol, etc.

Examples of coloring agents include those generally used in this field such as tar color, etc.

Various free-flow agents generally used in this field can be used, including light anhydrous silicic acid, etc.

A wide variety of lubricants generally used in this field can be used, including magnesium stearate, calcium stearate, polyoxyl stearate, talc, sucrose esters of fatty acid, dimethylpolysiloxane, etc.

Furthermore, it is possible to add flavors such as menthol and orange flavor to the sustained-release preparation of the present invention.

EFFECTS OF THE INVENTION

The present invention makes it possible to obtain a sustained-release preparation from which a pharmacologically active substance can be released for a long time.

According to the method of the present invention, use of an organic solvent is unnecessary, and this obviates the risk of adversely affecting on the human body, etc., during production or when administered.

The method of the present invention makes it possible to speedily obtain a preparation having an excellent sustained-release property.

BEST MODE FOR CARRYING OUT THE INVENTION

The present invention is explained in detail below with reference to Examples and Comparative Examples. Note that the components used below are as follows:

Component A (pharmacologically active substance): theophylline

Component B (low-melting-point substance),

B-1: glycerol behenate, product name: Poem B-200, manufactured by Riken Vitamin Co., Ltd.

B-2: tetraglycerol hexabehenate: product name Poem J-46B, manufactured by Riken Vitamin Co., Ltd. Component C (pH-independent water-insoluble polymer):

Ethylcellulose (average particle diameter of 3 to 15 μm, product name: Ethocel 7 cps Standard Premium, manufactured by Dow Chemical Company) Component D (fine powder), D-1: ethylcellulose (average particle diameter of 3 to 15 μm, product name: Ethocel 10 cps STD Premium (FP), manufactured by Dow Chemical Company)

D-2: talc (product name: MMR, manufactured by Asada Milling Co., Ltd.

D-3: talc (product name: JA-13R, manufactured by Asada Milling Co., Ltd.)

D-4: talc (product name: JA-24R, manufactured by Asada Milling Co., Ltd.)

D-5: magnesium stearate (manufactured by Taihei Chemicals Limited)

D-6: titanium oxide (manufactured by Fuji Talc Industrial Co, Ltd.) Other component E-1: light anhydrous silicic acid (product name: Adsolider 101, manufactured by Freund Industrial Co., Ltd.)

Examples 1-5

Glycerol behenate (Component B, B-1, 2200 g) was melted by heating to about 130° C., and 400 g of ethylcellulose (component C) was added thereto and melted. Theophylline (component A, 1114.3 g) was added to the molten mixture and then dispersed.

The resulting dispersion was subjected to spray cooling using a spray cooler with a diameter of about 1.6 m (product name: OC-16, manufactured by Okawahara Kakohki Co., Ltd.). The particles produced were sized by passing them through a sieve having openings of 355 μm, obtaining particles (core particles) having an average particle diameter of about 130 μm.

The above-obtained core particles (50 g) were placed in stainless steel beakers each equipped with a four-bladed propeller, and ethylcellulose (Component D, D-1) was added thereto in the amounts shown in Table 1. While heating each stainless steel beaker at 73° C., the mixture of the particles and ethylcellulose was stirred by rotating the four-bladed propeller at 1300 rpm, conducting melt-coating. Thereafter, lactose was added thereto with stirring in the amounts as shown in Table 1, and the mixture was then cooled to obtain melt-coated particles. The particles produced were sized by passing them through a sieve having openings of 355 μm, obtaining preparations of the present invention having an average particle diameter of about 135 to about 150 μm.

TABLE 1

| | Example 1 | Example 2 | Example 3 | Example 4 | Example 5 |
|---|---|---|---|---|---|
| Core particle (g) | 50 | 50 | 50 | 50 | 50 |
| Ethylcellulose (g) | 7 | 8 | 9 | 13 | 20 |
| Lactose (g) | 10 | 10 | 10 | 16 | 5 |

Test Example 1

Figure 1:
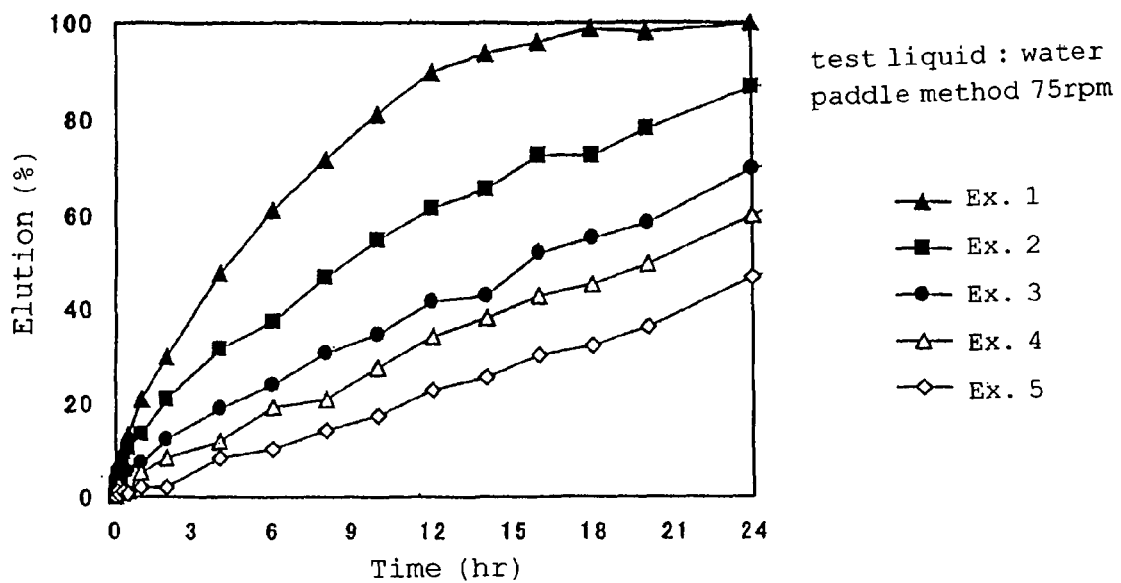
FIG. 1 is a graph showing the relationship between elapsed time and theophylline elution (%) of the pharmaceutical preparations obtained in Examples 1 to 5, tested immediately after production.

Immediately after being obtained, each preparation in Examples 1 to 5 (in an amount equivalent to a theophylline content of 100 mg) was added to 900 ml of purified water, and the extent of theophylline dissolution (%) was thereby measured in accordance with the paddle method of the dissolution test of the Japanese Pharmacopoeia $13^{th}$ revision (paddle revolutions: 75 rpm). The relationship between elapsed time after adding each preparation to the purified water and extent of dissolution was determined. FIG. 1 shows the results.

Comparative Example 1

Glycerol behenate (Component B, B-1, 2600 g) was melted by heating to about 120° C. and 1400 g of theophylline (component A) was added thereto and dispersed. The resulting dispersion was subjected to spray cooling using a spray cooler with a diameter of about 1.6 m (product name: OC-16, manufactured by Okawahara Kakohki Co., Ltd.). The particles produced were sized by passing them through a sieve having openings of 355 μm, obtaining particles (core particles) having an average particle diameter of about 110 μm.

The thus obtained particles (100 g) were then placed in a fluid-bed rotor granulator (product name: MP-01, manufactured by Powrex Corporation) and 100 g of ethylcellulose (Component D, D-1) was added. The mixture was fluidized under an air supply at 85° C., obtaining particles coated with ethylcellulose. The yield was 125 g and a loss of 75 g was recognized.

Examples 6-9

Glycerol behenate (Component B, B-1, 3.06 kg) was melted by heating to about 130° C., and 0.54 kg of ethylcellulose (Component C) was added thereto and then melted. Theophylline (Component A, 2.4 kg) was added to the molten mixture and dispersed.

The resulting dispersions were subjected to spray cooling using a spray cooler with a diameter of about 1.6 m (product name: OC-16, manufactured by Okawahara Kakohki Co., Ltd.). The particles produced were sized by passing them through a sieve having openings of 355 μm, obtaining particles (core particles) having an average particle diameter of about 140 μm.

The above-obtained core particles (50 g) were placed in stainless steel beakers each equipped with a four-bladed propeller, and ethylcellulose (Component D, D-1) and talc (Component D, D-2) were added thereto in the amounts shown in Table 2. While heating each stainless steel beaker at 70° C., the mixture of the particles, ethylcellulose and talc was stirred by rotating the four-bladed propeller at 1400 rpm, conducting melt-coating. Thereafter, lactose was added thereto with stirring in the amount shown in Table 2, and the mixture was then cooled to obtain melt-coated particles. The particles produced were sized by passing them through a sieve having openings of 355 μm, obtaining preparations of the present invention having an average particle diameter of about 140 to about 155 μm.

TABLE 2

| | Example 6 | Example 7 | Example 8 | Example 9 |
|---|---|---|---|---|
| Core particle (g) | 50 | 50 | 50 | 50 |
| Ethylcellulose (g) | 10 | 10 | 10 | 10 |
| Talc (g) | 1 | 2 | 4 | 6 |
| Lactose (g) | 10 | 10 | 10 | 10 |

Test Example 2

Figure 2:
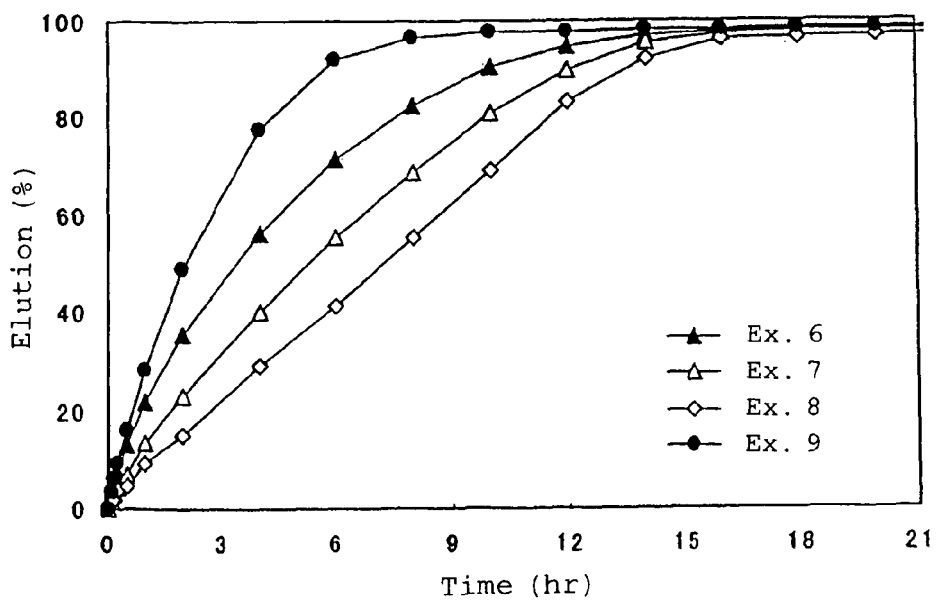
FIG. 2 is a graph showing the relationship between elapsed time and theophylline elution (%) of the pharmaceutical preparations obtained in Examples 6 to 9, tested immediately after production.

Immediately after being produced, each preparation in Examples 6 to 9 (in an amount equivalent to a theophylline content of 100 mg) was added to 900 ml of 0.2% sodium lauryl sulfate aqueous solution, and the extent of theophylline dissolution (%) was measured in accordance with the paddle method of the dissolution test of the Japanese Pharmacopoeia $13^{th}$ revision (paddle revolutions: 75 rpm). The relationship between elapsed time after adding the preparations to the sodium lauryl sulfate aqueous solution and extent of dissolution was thereby determined. FIG. 2 shows the results.

Example 10

Core particles (50 g) obtained in Examples 6 to 9 were placed in stainless steel beakers each equipped with a four-bladed propeller, and 10 g of ethylcellulose (Component D, D-1) was added thereto. While heating each stainless steel beaker at 70° C., the mixture of the particles and ethylcellulose was stirred by rotating the four-bladed propeller at 1400 rpm, conducting melt-coating. Thereafter, 10 g of lactose was added thereto with stirring, and the mixture was then cooled to obtain melt-coated particles. The particles produced were sized by passing them through a sieve having openings of 355 μm, obtaining preparations of the present invention having an average particle diameter of about 150 μm.

Comparative Example 2

Melt-coated particles were obtained in the same manner as in Example 10 except that 12 g of talc (D-2) was used as Component D instead of ethylcellulose. The particles were sized by passing them through a sieve having openings of 355 μm, obtaining preparations having an average particle diameter of about 127 μm.

Comparative Example 3

Melt-coated particles were obtained in the same manner as in Example 10 except that 12 g of talc (D-3) was used as Component D instead of ethylcellulose. The particles were sized by passing them through a sieve having openings of 355 μm, obtaining preparations having an average particle diameter of about 130 μm.

Comparative Example 4

Melt-coated particles were obtained in the same manner as in Example 10 except that 12 g of talc (D-4) was used as Component D instead of ethylcellulose. The particles were sized by passing them through a sieve having openings of 355 μm, obtaining preparations having an average particle diameter of about 126 μm.

Test Example 3

Figure 3:
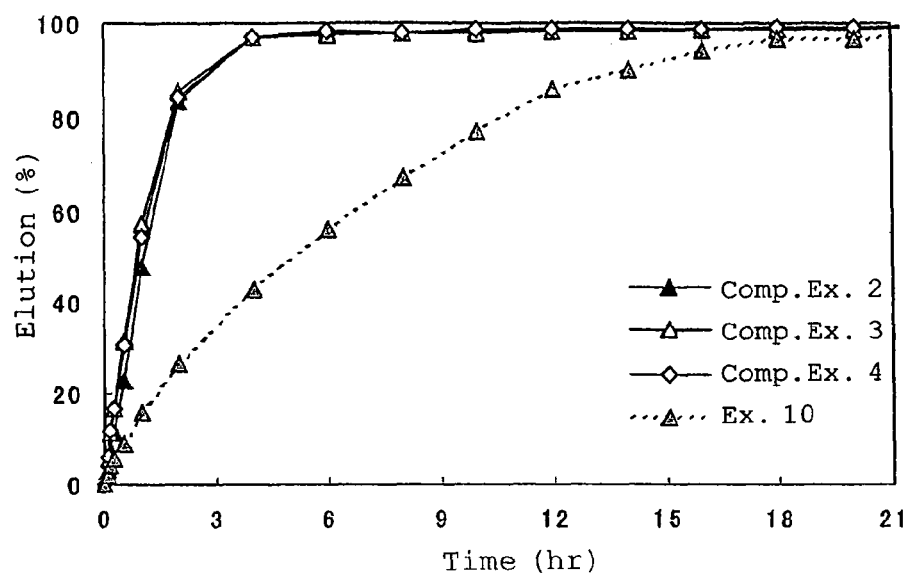
FIG. 3 is a graph showing the relationship between elapsed time and theophylline elution (%) of the pharmaceutical preparations obtained in Example 10 and Comparative Examples 2 to 4, tested immediately after production.

Immediately after being produced, each preparation in Example 10 and Comparative Examples 2 to 4 (in an amount equivalent to a theophylline content of 100 mg) was added to 900 ml of 0.2% sodium lauryl sulfate aqueous solution, and the extent of theophylline dissolution (%) was measured in accordance with the paddle method of the dissolution test of the Japanese Pharmacopoeia 13$^{th}$ revision (paddle revolutions: 75 rpm). The relationship between elapsed time after adding the preparations to the sodium lauryl sulfate aqueous solution and extent of dissolution was thereby determined. FIG. 3 shows the results.

As is clear from FIG. 3, the elution of theophylline cannot be controlled when melt-coating is conducted using 12 g of talc, whose amount is more than that of ethylcellulose, i.e., 10 g, and therefore it was impossible to obtain sustained-release preparations.

Example 11

Core particles (average particle size of about 140 μm, 50 g) obtained in Example 6 were placed in a stainless steel beaker equipped with a four-bladed propeller and 10 g of ethylcellulose (Component D, D-1), 1.5 g of talc (Component D, D-2) and 0.5 g of magnesium stearate (Component D, D-5) were added thereto. While heating the stainless steel beaker at 70° C., the mixture of the particles, ethylcellulose, talc and magnesium stearate was stirred by rotating the four-bladed propeller at 1400 rpm, conducting melt-coating. Thereafter, 3.8 g of talc and 0.2 g of magnesium stearate of the same kinds as used above were added thereto with stirring, and the mixture was then cooled to obtain melt-coated particles. The particles produced were sized by passing them through a sieve having openings of 355 μm, obtaining preparations of the present invention having an average particle diameter of about 134 μm.

Example 12

Core particles (average particle size of about 140 μm, 50 g) obtained in Example 6 were placed in a stainless steel beaker equipped with a four-bladed propeller and 10 g of ethylcellulose (Component D, D-1) and 3 g of magnesium stearate (Component D, D-5) were added thereto. While heating the stainless steel beaker at 70° C., the mixture of the particles, ethylcellulose and magnesium stearate was stirred by rotating the four-bladed propeller at 1400 rpm, conducting melt-coating. Thereafter, 1 g of magnesium stearate of the same kind as used above and 2 g of talc (D-2) were added thereto with stirring, and the mixture was then cooled to obtain melt-coated particles. The particles produced were sized by passing them through a sieve having openings of 355 μm, obtaining preparations of the present invention having an average particle diameter of about 135 μm.

Example 13

Glycerol behenate (component B, B-1, 3.25 kg) was melted by heating to about 120° C., and 1.75 kg of theophylline (component A) was added thereto and dispersed.

The resulting dispersion was subjected to spray cooling using a spray cooler having a diameter of about 1.6 m (product name: OC-16, manufactured by Okawahara Kakohki Co., Ltd.). The particles produced were sized by passing them through sieves having openings of 75 μm and 355 μm, obtaining particles having an average particle diameter of about 110 μm.

The above-obtained core particles (50 g) were placed in a stainless steel beaker equipped with a four-bladed propeller and 12 g of ethylcellulose (Component D, D-1) and 3 g of talc (Component D, D-2) were added thereto. While heating the stainless steel beaker to 73° C., the mixture of the particles, ethylcellulose and talc was stirred by rotating the four-bladed propeller at 1300 rpm, conducting melt-coating. Further talc (4 g) of the same kind as used above was added thereto while stirring, and the mixture was then cooled to obtain melt-coated particles. The particles produced were sized by passing them through a sieve having openings of 355 μm, obtaining preparations of the present invention having an average particle diameter of about 115 μm.

Example 14

Glycerol behenate (component B, B-1, 3.06 kg) was melted by heating to about 135° C., and 0.54 kg of ethylcellulose (Component C) was added thereto and melted. Theophylline (component A, 2.4 kg) was added thereto and dispersed.

The resulting dispersion was subjected to spray cooling using a spray cooler having a diameter of about 1.6 m (product name: OC-16, manufactured by Okawahara Kakohki Co., Ltd.). The particles produced were sized by passing them through sieves having openings of 75 μm and 355 μm, obtaining particles having an average particle diameter of about 100 μm.

The above-obtained core particles (50 g) were placed in a stainless steel beaker equipped with a four-bladed propeller and 10 g of ethylcellulose (Component D, D-1), 1 g of talc (Component D, D-2) and 5 g of titanium oxide were added thereto. While heating the stainless steel beaker at 71° C., the mixture of the particles, ethylcellulose, talc and titanium oxide was stirred by rotating the four-bladed propeller at 1400 rpm, conducting melt-coating. Thereafter, 3.8 g of talc of the same kind as used above and 0.2 g of magnesium stearate (D-5) were added thereto with stirring, and the mixture was then cooled to obtain melt-coated particles. The particles produced were sized by passing them through a sieve having openings of 355 μm, obtaining preparations of the present invention having an average particle diameter of about 104 μm.

Example 15

Core particles (50 g) obtained in Example 14 were placed in a stainless steel beaker equipped with a four-bladed propeller and 11 g of ethylcellulose (Component D, D-1) and 3 g of talc (Component D, D-2) were added thereto. While heating the stainless steel beaker at 71° C., the mixture of the particles, ethylcellulose and talc was stirred by rotating the four-bladed propeller at 1400 rpm, conducting melt-coating. Thereafter, 3.8 g of talc of the same kind as used above and 0.2 g of magnesium stearate (D-5) were added thereto with stirring, and the mixture was then cooled to obtain melt-coated particles. The particles produced were sized by passing them through a sieve having openings of 355 μm, obtaining preparations of the present invention having an average particle diameter of about 110 μm.

Test Example 4

Using each preparation immediately after being obtained in Examples 11 to 15 (in an amount equivalent to a theophylline content of 100 mg), the extent of theophylline dissolution (%) was measured in accordance with the paddle method of the dissolution test of the Japanese Pharmacopoeia 13$^{th}$ revision (paddle revolutions: 75 rpm).

As a result, the preparations obtained in Examples 11 to 15 exhibited excellent sustained-release properties.

Example 16

Core particles (800 g) obtained in Example 1, 112 g of ethylcellulose (Component D, D-1) and 56 g of talc (Component D, D-2) were placed in a high-speed granulator mixer equipped with a jacket (product name: FM-VG-05, manufactured by Powrex Corporation). While maintaining the jacket temperature at about 68 to 70° C., the mixture was stirred at a blade rotation speed of 300 to 500 rpm, and when the amounts of the ethylcellulose and talc became small, 112 g of ethylcellulose (D-1) and 56 g of talc (D-2) were placed therein and the heating and stirring were continued. When no ethylcellulose and talc were left, 56 g of talc (D-2) was added thereto and stirring was continued. When no talc was left, temperature of the jacket of the high-speed granulator mixer was lowered, and the mixture was cooled with stirring, obtaining melt-coated particles.

The thus obtained melt-coated particles were removed from the high-speed granulator mixer, and 0.8 g of light anhydrous silicic acid (E-1) was added to the particles. The particles were sized by passing them through a sieve having openings of 355 μm, obtaining preparations of the present invention having an average particle diameter of about 157 μm.

Example 17

Core particles (750 g) obtained in Example 1, 105 g of ethylcellulose (Component D, D-1) and 35 g of talc (Component D, D-2) were placed in a high-speed granulator mixer equipped with a jacket (product name: FM-VG-05, manufactured by Powrex Corporation). While maintaining the jacket temperature at about 68-70° C., the mixture was stirred at a blade rotation speed of 300-500 rpm, and when the amounts of the ethylcellulose and talc became small, 105 g of ethylcellulose (D-1) and 35 g of talc (D-2) were placed therein and the heating and stirring were continued. When no ethylcellulose and talc were left, 52.5 g of talc (D-2) was added thereto and stirring was continued. When no talc was left, the temperature of the jacket of the high-speed granulator mixer was lowered, and the mixture was cooled with stirring, obtaining melt-coated particles.

The thus obtained melt-coated particles were removed from the high-speed granulator mixer, and 0.75 g of light anhydrous silicic acid (E-1) was added to the particles. The particles were sized by passing them through a sieve having openings of 355 μm, obtaining preparations of the present invention having an average particle diameter of about 152 μm.

Example 18

The core particles (750 g) obtained in Example 1, 105 g of ethylcellulose (Component D, D-1) and 26.3 g of talc (Component D, D-2) were placed in a high-speed granulator mixer equipped with a jacket (product name: FM-VG-05, manufactured by Powrex Corporation). While maintaining the jacket temperature at about 68-70° C., the mixture was stirred at a blade rotation speed of 300-500 rpm, and when the amounts of the ethylcellulose and talc became small, 105 g of ethylcellulose (D-1) and 26.3 g of talc (D-2) were placed therein and the heating and stirring were continued. When no ethylcellulose and talc were left, 52.5 g of talc (D-2) was added thereto and stirring was continued. When no talc was left, the temperature of the jacket of the high-speed granulator mixer was lowered, and the mixture was cooled with stirring, obtaining melt-coated particles.

The thus obtained melt-coated particles were removed from the high-speed granulator mixer, and 0.75 g of light anhydrous silicic acid (E-1) was added to the particle. The particles were sized by passing them through a sieve having openings of 355 μm, obtaining preparations of the present invention having an average particle diameter of about 140 μm.

Example 19

Glycerol behenate (Component B, B-1, 1710 g) and tetraglycerol hexabehenate (Component B, B-2, 1710 g) were melted by heating to about 130° C., and 180 g of ethylcellulose (component C) was added thereto and melted. Theophylline (Component A, 2400 g) was added thereto and dispersed.

The resulting dispersion was subjected to spray cooling and sizing in the same manner as in Example 1, obtaining particles (core particles) having an average particle diameter of about 137 μm.

Thereafter, the above-obtained core particles (50 g) were placed in a stainless steel beaker equipped with a four-bladed propeller and 7 g of ethylcellulose (Component D, D-1) and 11 g of talc (Component D, D-2) were added thereto. While heating the stainless steel beaker at 70° C., the mixture of the particles, ethylcellulose and talc was stirred by rotating the four-bladed propeller at 1400 rpm, conducting melt-coating. Thereafter, 5 g of talc (D-2) was added thereto with stirring, and the mixture was then cooled to obtain melt-coated particles. Light anhydrous silicic acid (E-1, 0.05 g) was added thereto, the particles produced were sized by passing them through a sieve having openings of 355 μm, obtaining preparations of the present invention having an average particle diameter of about 140 μm.

Test Example 5

Using each preparation immediately after being obtained in Examples 16 to 19, the extent of theophylline dissolution (%) was measured in accordance with the paddle method of the dissolution test of the Japanese Pharmacopoeia 13$^{th}$ revision (paddle revolutions: 75 rpm) in the same manner as in Test Example 3.

Figure 4:
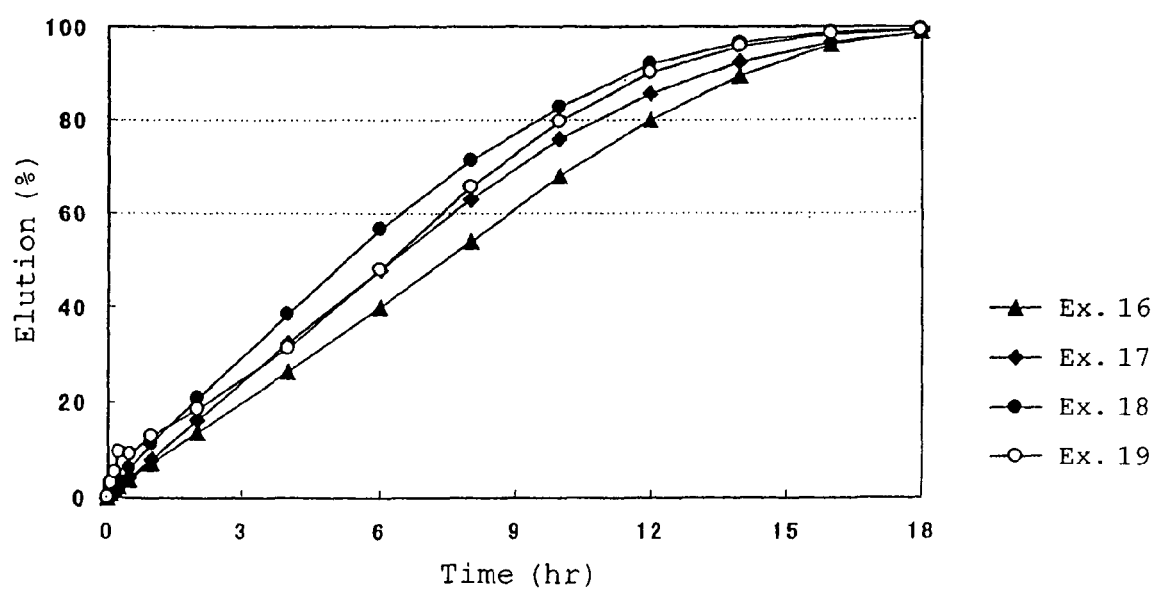
FIG. 4 is a graph showing the relationship between the elapsed time and the theophylline elution (%) of the pharmaceutical preparations obtained in Examples 16 to 19, tested immediately after production.

The relationship between elapsed time after adding the preparations to 0.2% sodium lauryl sulfate aqueous solution and extent of dissolution was thereby determined. FIG. 4 shows the results.

The invention claimed is:

1. A sustained-release preparation, which is obtained by dissolving or dispersing a pharmacologically active substance in a molten mixture of a low-melting-point substance and a pH-independent water-insoluble polymer; spraying and cooling the resulting liquid to obtain particles; melt-coating the surface of the thus obtained particles with (1) a fine powder of ethylcellulose or (2) a fine powder of ethylcellulose and at least one member selected from the group consisting of talc, magnesium stearate and titanium oxide, the content of the ethylcellulose in the fine powder being not less than 60 wt %; and adhering a powder of at least one member selected from the group consisting of lactose, talc, magnesium stearate and titanium oxide to the melt-coated surface;

the low-melting-point substance being at least one member selected from the group consisting of glycerol fatty acid esters, polyglycerol fatty acid esters, glycerol fatty acids and citric acid, stearic acid, palmitic acid, stearyl alcohol, and cetanol; and the pH-independent water-insoluble polymer being at least one member selected from the group consisting of ethylcellulose, aminoalkyl methacrylate copolymer RS, aminoalkyl methacrylate copolymer RL, cellulose acetate, cellulose acetate butyrate, and cellulose acetate propionate; and the content of the pH-independent water-insoluble polymer in the molten mixture being 0.5 to 60 wt. % relative to the low-melting-point substance.

2. A method for producing a sustained-release preparation of claim 1 comprising the steps of:

dissolving or dispersing a pharmacologically active substance in a molten mixture of a low-melting-point substance, which is at least one member selected from the group consisting of glycerol fatty acid esters, polyglycerol fatty acid esters, glycerol fatty acids and citric acid, stearic acid, palmitic acid, stearyl alcohol, and cetanol and a pH-independent water-insoluble polymer, which is at least one member selected from the group consisting of ethylcellulose, aminoalkyl methacrylate copolymer RS, aminoalkyl methacrylate copolymer RL, cellulose acetate, cellulose acetate butyrate, and cellulose acetate propionate, the molten mixture containing the pH-independent water-insoluble polymer in the molten mixture in an amount of 0.5 to 60 wt. % relative to the low-melting-point substance;

spraying and cooling the resulting liquid to obtain particles;

melt-coating the surface of the thus obtained particles with (1) a fine powder of ethylcellulose or (2) a fine powder of ethylcellulose and at least one member selected from the group consisting of talc, magnesium stearate and titanium oxide, the content of the ethylcellulose in the fine powder being not less than 60 wt %; and adhering to the thus-formed melt-coated surface with a powder of at least one member selected from the group consisting of lactose, talc, magnesium stearate and titanium oxide.

* * * * *